(12) United States Patent
Freire et al.

(10) Patent No.: US 6,242,190 B1
(45) Date of Patent: *Jun. 5, 2001

(54) METHOD FOR HIGH THROUGHPUT THERMODYNAMIC SCREENING OF LIGANDS

(75) Inventors: Ernesto Freire, Baltimore, MD (US); Matthew J. Todd, Newark, DE (US)

(73) Assignee: John Hopkins University, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/451,837

(22) Filed: Dec. 1, 1999

(51) Int. Cl.[7] .......................................... C12Q 1/68
(52) U.S. Cl. ..................... 435/6; 435/3; 435/4; 435/5; 435/7.1; 435/7.9; 435/7.92
(58) Field of Search .................... 435/3, 4, 5, 6, 435/7.1, 7.9, 7.92

(56) References Cited

U.S. PATENT DOCUMENTS 5,518,882 * 5/1996 Lund et al. .............................. 435/6

* cited by examiner

*Primary Examiner*—James Housel
*Assistant Examiner*—Brett Nelson
(74) *Attorney, Agent, or Firm*—McGuire Woods, LLP

(57) ABSTRACT

The present invention provides a method of rapidly screening ligands on the basis of their binding affinity and binding enthalpy by carrying out binding assays at a minimum of two temperatures. This technique permits the selection for further optimization of lead ligands that bind to the target molecules with favorable enthalpies. Those ligands will exhibit higher solubilities in aqueous solution than ligands selected by conventional means, and may exhibit lower susceptibilities to resistant mutations. The method may be utilized as a standalone technique, or may be adapted to, for example, known high throughput screening technologies. The present invention further comprises an apparatus for carrying out the described methods.

8 Claims, 3 Drawing Sheets

1. PLACE MACROMOLECULE IN THE WELLS OF A MULTIWELL PLATE.

2. ADD CANDIDATE LIGANDS TO WELLS: INCUBATE PLATES AT TWO DIFFERENT TEMPERATURES.

3. DETECT BOUND LIGAND

4. SELECT AS "LEAD LIGAND" CANDIDATE LIGAND WHICH DISPLAYS DECREASED BINDING AFFINITY AT HIGHER TEMPERATURE.

METHOD FOR HIGH THROUGHPUT THERMODYNAMIC SCREENING OF LIGANDS

This invention was made using funds from grants from the National Institutes of Health having grant number GM 57144. The government may have certain rights in this invention.

BACKGROUND OF THE INVENTION

1. Field of the Invention

The invention generally relates to the screening of ligands on the basis of their binding affinity and binding enthalpy. In particular, the invention provides a method to identify ligands that bind to a target macromolecule with favorable enthalpies by carrying out high throughput screening techniques at a minimum of two different temperatures.

2. Background of the Invention

The identification of drug candidates by screening large libraries of potential lead compounds and their optimization by structure-based design is an important component in the development of new pharmaceutical drugs. Modern high throughput screening procedures are able to process thousands of compounds and identify those that exhibit the highest binding affinity with relative accuracy. The binding affinity, Ka, is defined in terms of the free energy of binding:

$$Ka = e^{-\Delta G/RT} \quad (1)$$

where R is the gas constant and T the absolute temperature. The free energy of binding is in turn defined by the enthalpy ($\Delta H$) and entropy ($\Delta S$) changes:

$$\Delta G = \Delta H - T\Delta S \quad (2)$$

therefore, $$Ka = e^{-(\Delta H - T\Delta S)/RT}$$

or, $$Ka = e^{-\Delta H/RT} \times e^{\Delta S/R} \quad (3)$$

It is evident that the binding affinity can be optimized by making $\Delta H$ more negative, $\Delta S$ more positive or by a combination of both. Even though compounds with many different combinations of $\Delta H$ and $\Delta S$ values will exhibit the same binding affinity (i.e. the same $\Delta G$ and therefore the same Ka), the properties and the response of these compounds to changes in the environment or in the protein target are not the same. The binding enthalpy reflects the interactions of the ligand with the target protein (e.g., van der Waals, hydrogen bonds, etc.). The entropy change, on the other hand, reflects two main contributions: changes in solvation entropy and changes in conformational entropy. Upon binding, desolvation occurs, water is released and a gain in solvent entropy is observed. This gain is particularly important for hydrophobic groups. At the same time, the ligand (and certain groups in the protein) lose conformational freedom resulting in a negative change in conformational entropy. Accordingly, there are three main strategies for improving binding affinity: 1) Improving ligand protein interactions over those with the solvent in order to obtain a negative enthalpy change; 2) Making the ligand more hydrophobic in order to make the solvation entropy large and positive; and, 3) Pre-shaping the ligand to the geometry of the binding site in order to minimize the loss of conformational entropy upon binding. Of these three strategies the easier to implement in structure-based drug design have been 2) and 3). As a result, the majority of affinity-optimized drug candidates are entropy optimized and thus are highly hydrophobic and rigid (pre-shaped to the geometry of the binding site).

Highly hydrophobic, rigid molecules have several drawbacks as potential drugs. First, they are highly insoluble in aqueous solution making their administration difficult. Second, rigidity reduces their ability to accommodate to changes in the geometry of the binding site, increasing their susceptibility to drug resistant mutations in the target protein. The correlation between lack of flexibility and susceptibility to resistant mutants has been recently brought into light for HIV-I protease inhibitors and for HIV-I reverse transcriptase inhibitors.

It is evident that flexible ligands will be less susceptible to resistant mutations. However, introducing flexibility in existing ligands will lower their binding affinity because of the larger conformational entropy loss upon binding. The introduction of flexibility needs to be compensated by the introduction of additional favorable interactions. These interactions cannot be hydrophobic because flexible hydrophobic ligands will lack specificity and, in addition, ligand candidates in current databases already favor hydrophobic interactions. The solution is to improve their binding enthalpy. Since the favorable binding enthalpy originates from specific ligand/target interactions, an enthalpic optimization will provide the additional binding affinity and the necessary target specificity.

It is currently possible to obtain binding enthalpy data to be used in the selection of likely candidate ligands via isothermal titration calorimetry (ITC). However, such direct calorimetric titrations, while accurate, are extremely time consuming (~2 hours per compound) and thus cannot be incorporated into a fast screening protocol. Further, the instruments themselves are costly and require a high level of expertise to operate and maintain, making this technique unsuitable for rapid, high throughput ligand screening.

It would thus be highly desirable to have available a method and apparatus to screen multiple ligands rapidly and identify those with favorable enthalpies during the early stages of the screening procedure. These ligands would exhibit higher solubilities in aqueous solution, better specificity, and lower susceptibility to resistant mutations. Further, it would be advantageous if the method was readily adaptable to existing high throughput technologies.

SUMMARY OF THE INVENTION

It is an object of this invention to provide a rapid method for screening multiple ligands on the basis of binding enthalpy. The method can be coupled to existing high throughput screening technologies, or used as a standalone technique. The method encompasses exposing a macromolecule to a variety of potential candidate ligands and measuring the binding affinities of the ligands at a minimum of two different temperatures. The binding affinities exhibited by the candidate ligands at the various temperatures are then compared, and ligands exhibiting favorable enthalpies may be selected for further optimization.

Potential macromolecules for which ligands may be selected in this manner include a wide array of naturally occurring and synthetic macromolecules, including proteins, peptides, nucleic acids, carbohydrates, and receptor molecules. Ligands which are encompassed by the present invention include a wide array of naturally occurring and synthetic molecules, including proteins, peptides, nucleic acids, carbohydrates, enzyme substrates, and enzyme inhibitors.

The method of the present invention is applicable to a wide variety of high throughput ligand screening protocols, including incubation of the macromolecule and ligands in multiwell plates, in etched channels, in capillary tubes, on absorbent solid supports, and the like. Further, the binding affinities may be measured by the detection of any parameter which changes in either the macromolecule or the ligand as a result of ligand binding, either directly or indirectly, including fluorescence, luminescence, emission of light, absorbance of light, radioactivity, fluorescence resonance energy transfer (FRET), pH, enzymatic activity, molecular weight, antibody binding, etc.

It is a further object of the present invention to provide an apparatus capable of carrying out the method of the present invention. Such an apparatus includes a means for exposing the macromolecule to the candidate ligands at a minimum of two different temperatures. In addition, the apparatus may include a means to measure the binding affinities of the various ligands at all temperatures at which the binding reaction is carried out, and a means to analyze the data, including a means to store, display and mathematically manipulate the binding affinities.

DETAILED DESCRIPTION OF THE PREFERRED EMBODIMENTS OF THE INVENTION

Figure 1:
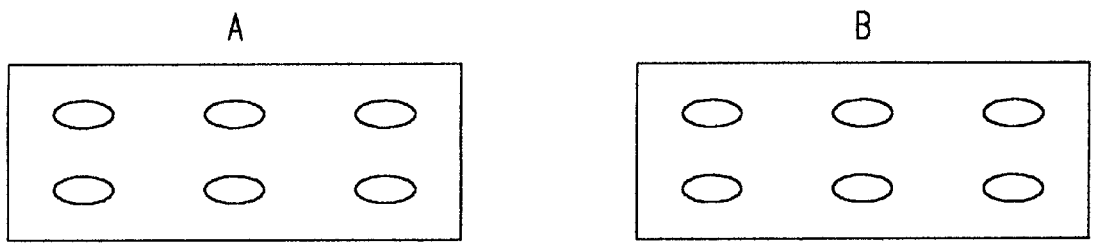
FIG. 1. Schematic of an Assay. Multiwell plates A and B contain immobilized macromolecule. Various candidate ligands are added to the duplicate plates and the plates are incubated at different temperatures. A lead ligand is selected based on the degree of binding at the different temperatures.
Figure 1:
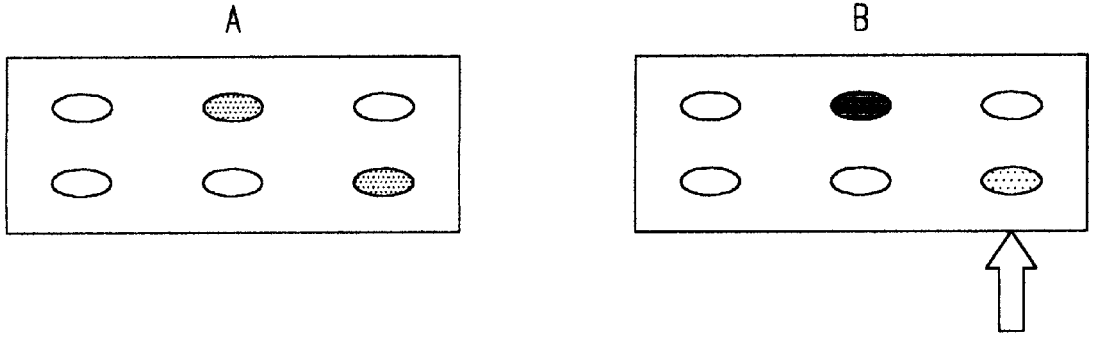

The present invention provides a method to screen multiple ligands rapidly on the basis of their binding affinity and binding enthalpy. The technology described here is designed to be used either as a standalone method, or it may be adapted for use with existing high throughput screening instruments.

In the practice of the present invention, the important quantity to be considered is the amount of ligand bound since this is the quantity measured directly or indirectly by any screening procedure. The amount of ligand bound $[L_B]$ is equal to the amount of target protein, $[P]$, multiplied by the degree of binding saturation, $F_B$:

$$[L_B] = [P] \times F_B \qquad (4)$$

where $[L_B]$ and $[P]$ are expressed in molar concentration units. Equation 4 can be written in terms of the binding affinity, Ka, and the free concentration of ligand, [L] as:

$$[L_B] = [P] \times n \times \frac{Ka[L]}{(1 + Ka[L])} \qquad (5)$$

where n is the number of binding sites in the target protein. n is usually one but can also be different than one. The affinity constant is a function of temperature (see equations 1–3). Moreover, the temperature dependence of Ka is dictated by the magnitude and sign of ΔH:

$$\frac{\delta \ln Ka}{\delta T} = \frac{\Delta H}{RT^2} \qquad (6a)$$

or $$\ln Ka = \frac{\Delta S}{R} - \frac{\Delta H}{RT} \qquad (6b)$$

If ΔH is positive the binding affinity will increase with temperature. Conversely, if ΔH is negative, the binding affinity will decrease with temperature. The net result is that in the first case the amount of bound ligand will increase with temperature whereas in the second case the amount of bound ligand will decrease with temperature. This temperature relationship provides the foundation for the method proposed here. The change in the concentration of bound ligand associated with a change in temperature is given by:

$$\frac{\delta[L_B]}{\delta T} = \frac{Ka[L]}{(1 + ka[L])^2} \times \frac{\Delta H}{RT^2} \qquad (7)$$

The methods proposed here are based upon the premise that ligands that bind to the target with lower affinity at higher temperatures are characterized by negative binding enthalpies (exothermic), whereas ligands that bind to the target with higher affinity at higher temperatures are characterized by positive binding enthalpies (endothermic).

A) Direct Binding Measurement

In a preferred embodiment of the present invention, a property (i.e. a physical observable) of the protein target that is sensitive to binding is used to measure the amount of ligand bound. Any appropriate property which is detectable and which is sensitive to ligand binding may be used in the practice of the present invention to measure the amount of ligand bound. In a preferred embodiment of the present invention, the property which is selected for detection is measurable on a time scale which is commensurate with high throughput screening. For example, this property may be optical absorbance, fluorescence emission, visible-range color changes, and the like. Those of skill in the art will recognize that many such suitable properties exist.

Those of skill in the art will recognize that many different types of screening technologies exist, or are under development, or may be developed, to which the methods of the present invention may be readily adapted. For example, assays which utilize multiwell plates, capillary tubes, solid supports, flow systems, standard cuvettes and the like, may be adapted for use in the practice of the present invention. Any technology which detects ligand binding may be adapted for use in the practice of the present invention. In preferred embodiments of the present invention, the technologies which are adapted are high throughput screening technologies.

In a preferred embodiment of the present invention, ligand binding is measured at a minimum of two temperatures. Those of skill in the art will recognize that the exact choice of temperatures at which to perform the measurements will vary from assay to assay, depending on the nature of the ligand and macromolecule, reagents, and availability of and limitations of suitable instrumentation. However, in general, the further apart the temperatures, the better the resolution of the data will be. In a preferred embodiment of the present invention, the temperatures selected should fall within the practically useful range of about 10° C. to about 40° C. Proteins tend to denature at higher temperatures, and at lower temperatures water condensation from the atmosphere may impede measurements. However, if, for example, the macromolecule is a protein which is known to be stable at very high temperatures (e.g. 90° C.), higher temperatures may be utilized. Further, if the instrumentation is equipped to operate under conditions in which condensation would not occur (e.g. under a stream of $N_2$) then temperatures lower than 10° C. may be employed. Any temperature range may be used so long as the integrity of ligand binding and measurement of the binding is not compromised.

In addition, the number of temperatures at which ligand binding is measured may be determined by the level of accuracy of data which is desired. For example, in some high throughput procedures where many candidate ligands are being screened, it may be adequate to do an initial screening at only two temperatures in order to select likely lead ligands for further work-up. Alternatively, if, for example, fewer ligands are to be screened but it is desired to obtain a more thorough and detailed analysis of their binding affinities, the ligands may be analyzed at several different temperatures and also under a variety of conditions (e.g. different concentrations of ligand or buffering components, or at different pH values) in order to characterize more fully the binding event. Those of skill in the art will recognize that the method of the present invention can be readily applied in a variety of ways to achieve various levels of detail with respect to ligand binding.

The magnitude and sign of the enthalpy change is evaluated from the variation of binding affinity or the variation in degree of binding associated with the temperature change. Those of skill in the art will recognize that the magnitude of the enthalpy change which would be considered significant will vary from ligand to ligand, from macromolecule to macromolecule, and on the accuracy of the technique used to do the measurements. However, on average, enthalpy differences as small as 2 kcal/mol should be observable by most techniques and may be considered significant.

A simplified direct binding assay performed according to the methods of the present invention is depicted in FIG. 1. As can be seen, a macromolecule (for example, a protein) is placed in the wells of two duplicate multiwell plates, A and B. Candidate ligands are added to the corresponding wells of both plates, and the two plates are incubated at different temperatures. (Note that for simplicity of illustration, no duplicate or control wells are included in FIG. 1.) After an appropriate time period, bound ligand is detected by some suitable means. In FIG. 1, the binding of the two positive ligands appears to be identical at the lower temperature (Plate A). By analyzing data at this single temperature (which would be the current practice) it is not possible to distinguish which positive ligand has a more favorable binding enthalpy and would thus be preferred for further work-up. However, the results obtained at the higher temperature (Plate B) show that one of the two positive ligands (indicated by the arrow) binds less well at the higher temperature, indicating that its binding is favorable enthalpically. According to the practice of the present invention, this enthalpically favorable ligand would be selected as the preferred lead ligand.

Figure 2:
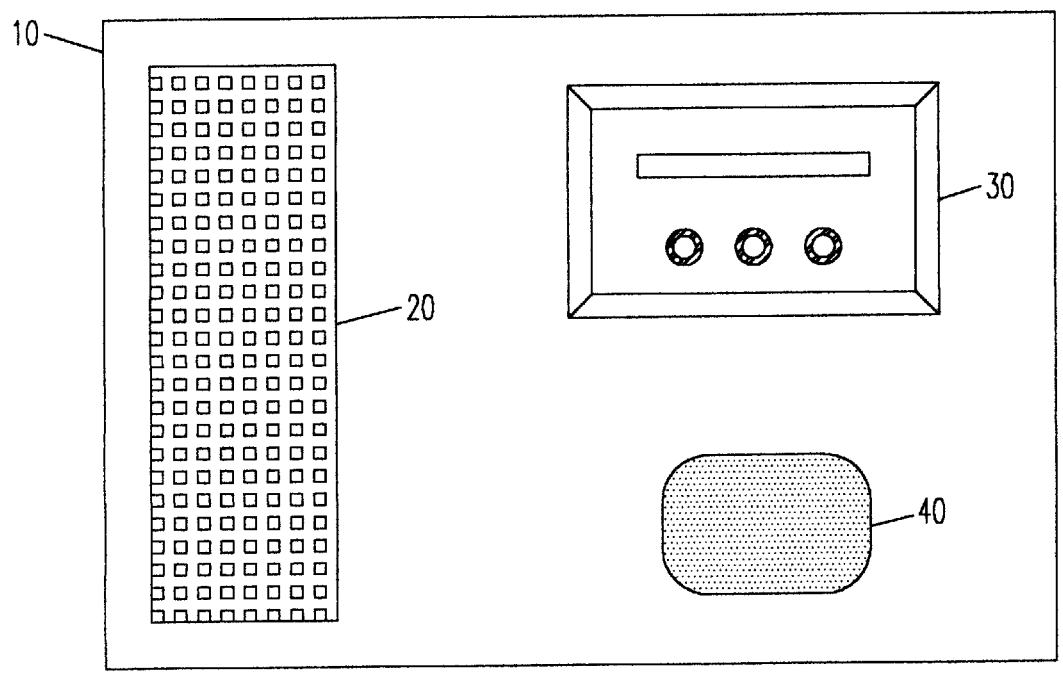
FIG. 2. Schematic of an Apparatus. An apparatus (10) for carrying out the methods of the present invention includes a temperature-regulatable assay module (20), and may include a means for measuring binding (30) and a means for storing, displaying and mathematically manipulating the data which is obtained (40).

The present invention also includes an apparatus designed to carry out the practice of the present invention. Many different configurations of instrumentation may be employed in the apparatus of the present invention. A schematic illustration of such an apparatus is given in FIG. 2. The apparatus (10) includes a temperature-regulatable assay module (20) with means for exposing samples of a macromolecule to ligands. The apparatus may further include on-board means for measuring binding affinities (30), by detecting a change associated with ligand binding, for example, a fluorescence detector. Alternatively, the means 30 for measuring binding affinities may be located outside the apparatus. The apparatus 10 may further include a means (40) for storing, displaying and mathematically manipulating the measured binding affinities, for example a computer and software. Alternatively, means 40 or components thereof may be located outside the apparatus 10. Means 40 may be interfaced with other components of apparatus 10, for example assay module 20 and/or measuring means 30. The apparatus 10 of the present invention may further include such features as automatic pipettors, conveyor belts, robotic arms, and the like (not illustrated) in order to further automate the apparatus 10.

b) Coupling to Enzyme Activity Measurements

Those of skill in the art will recognize that the method of the present invention may be used to detect any type of ligand binding. In a preferred embodiment of the present invention, the method of the present invention may be coupled to enzyme activity measurements. In this case, an effect triggered by the binding of a ligand, for example an enzyme inhibitor, is used to follow the binding reaction. The development of enzyme inhibitors is particularly attractive for drug development. For enzyme inhibitors, the binding is not necessarily measured directly but rather by measuring the inhibitory effect of the ligand. In general, enzyme velocity is calculated by measuring the amount of substrate depleted or product formed after a certain specified time interval. In the method presented here, enzyme activity measurements are performed at a minimum of two temperatures and the initial velocities are measured in the absence and in the presence of a known concentration of inhibitor. A decrease in the amount of substrate depleted or product formed is indicative of an increase in the amount of inhibitor bound.

The initial velocity v(I) in the presence of a concentration [I] of inhibitor is given by standard rate equations. It can be shown that at low substrate concentrations ([S]<<Km), both competitive and non-competitive inhibitors will exhibit the same apparent kinetic behavior. For competitive inhibition:

$$v(I) = \frac{k_{cat}[S]}{Km\left(1 + \frac{[I]}{K_I}\right) + [S]} \approx \frac{k_{cat}[S]}{Km\left(1 + \frac{[I]}{K_I}\right)} \tag{8}$$

and for non-competitive inhibition:

$$v(I) = \frac{k_{cat}[S]}{Km\left(1 + \frac{[I]}{K_I}\right) + [S]\left(1 + \frac{[I]}{K_I}\right)} \approx \frac{k_{cat}[S]}{Km\left(1 + \frac{[I]}{K_I}\right)} \tag{9}$$

The above equations indicate that the observed rate v(I) is dependent on several kinetic parameters that can be affected by temperature. Therefore, the effect of temperature on the inhibition constant, $K_I$, must be isolated from the temperature effects on the other parameters. This can be done by normalizing the measured activity to that obtained in the absence of the inhibitor. The relative decrease in activity due to the presence of inhibitor v(I)/v(O) is simply:

$$\frac{v(I)}{v(O)} = \frac{K_r}{(K_I + [I])} \quad (10)$$

indicating that under these conditions, the temperature dependence of K, can be isolated from that of Km. According to the above equations, measuring v(I)/v(O) at several temperatures under conditions in which the substrate concentration is much lower than Km will give the enthalpic contribution to inhibitor binding. In this way, the temperature effects on the binding of substrate can be separated from the effects on the binding of the inhibitors.

Thus, the methods of the present invention provide the necessary information to implement a screening protocol that provides both binding affinities and binding enthalpies for potential ligands.

The results demonstrated in the Examples section below show that fast screening methods need not be restricted to determining binding affinity alone, but that by performing the experimental screening of potential inhibitors at a minimum of two temperatures it is also possible to identify lead compounds according to the sign and magnitude of their binding enthalpies. Knowledge of these binding parameters adds a new dimension to the process of drug design.

EXAMPLES

Example 1

Figure 3A:
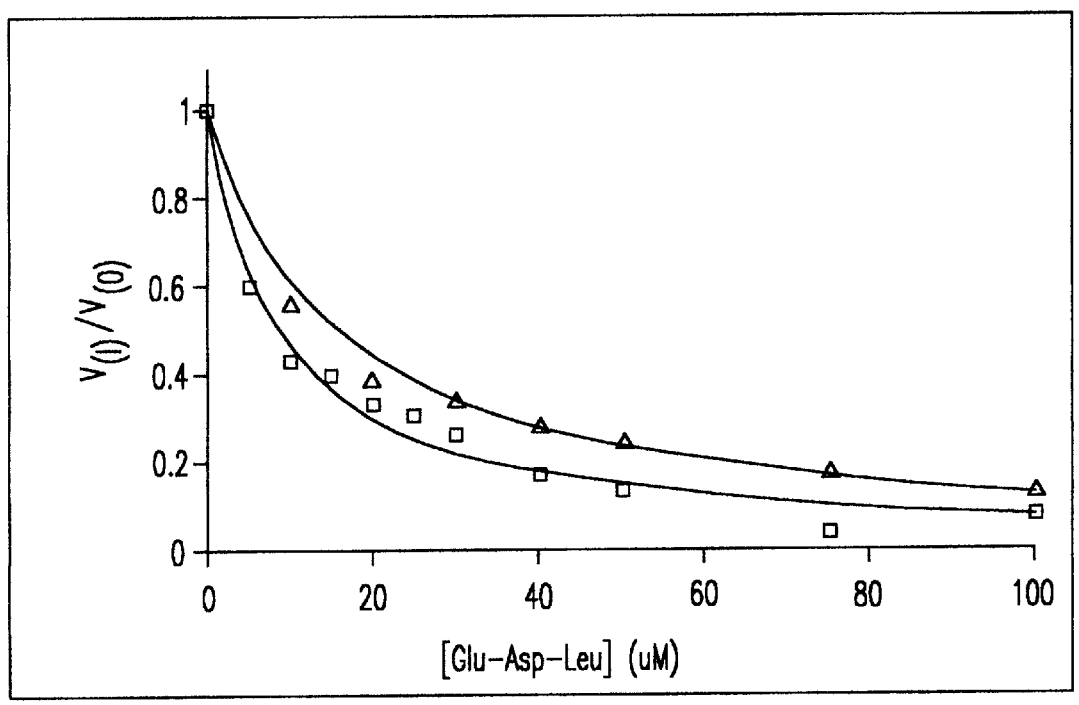
FIG. 3. Temperature dependence of HIV-protease inhibition for an exothermic and endothermic inhibitor. Fractional activity, measured at increasing concentrations of Glu-Asp-Leu (FIG. 3A) or Acetyl-pepstatin (FIG. 3B), were determined at 15° C. (solid squares) or 35° C. (open triangles).
Figure 3B:
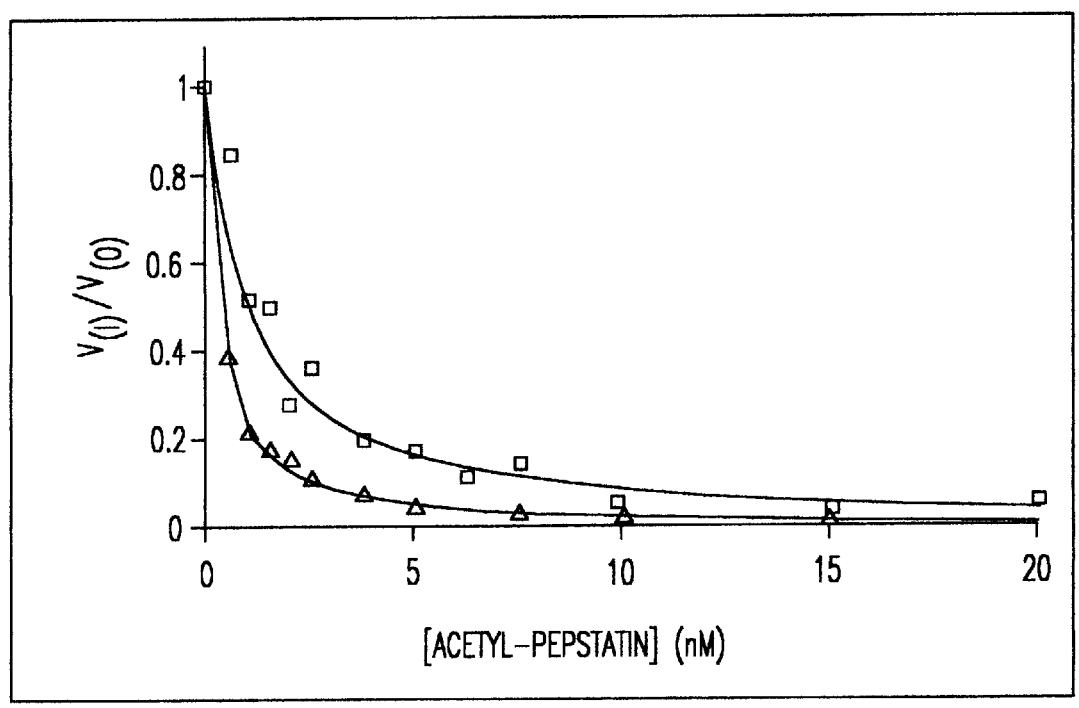

In order to test the accuracy of the above mathematical treatment, the enzymatic activity of the HIV-1 protease was measured in the presence of two different inhibitors, acetyl pepstatin and Glu-Asp-Leu. Fractional activity, measured at increasing concentrations of Glu-Asp-Leu (FIG. 3A) or Acetyl-pepstatin (FIG. 3B), was determined at 15° C. (solid squares) and at 35° C. (open triangles). The inhibition by Acetyl-pepstatin was measured in 10 mM NaOAc, pH 5.0, using 50 μM chromogenic substrate. The inhibition by Glu-Asp-Leu was measured in 10 mM sodium Formate, pH 3.5 using 40 μM substrate. In both cases [S]<<K=2.5 mM.

FIG. 3 shows the results of these experiments. As can be seen, the binding affinity of Glu-Asp-Leu is lower at 35° C. than at 15° C. whereas acetyl pepstatin exhibits a higher affinity at 35° C. Analysis of the data in terms of equation 10 (solid lines) yields inhibition constants of 9 and 16 μM for Glu-Asp-Leu; and 1 and 0.3 μM for acetyl pepstatin at 15° C. and 35° C., respectively. As expected, the binding affinity decreases at higher temperatures for the exothermic inhibitor and increases for the endothermic inhibitor.

The binding enthalpies calculated from the data in FIG. 3 using equation 6b, are −5 and 10.5 kcal/mol for Glu-Asp-Leu and acetyl pepstatin respectively, which are close to the values measured directly by calorimetric titrations (−3.6 and 7.3 kcal/mol respectively).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for screening candidate ligands in order to select enthalpically favorable lead ligands, wherein said enthalpically favorable lead ligands exhibit a negative ΔH, comprising the steps of:

carrying out steps a–c for a plurality of said candidate ligands, wherein said steps a–c are:
   a) exposing a macromolecule to a ligand at a plurality of temperatures;
   b) measuring a binding affinity of said macromolecule for said ligand at each of said plurality of temperatures, thereby generating a plurality of binding affinity values, each of which is associated with one of said plurality of temperatures; and,
   c) evaluating said ΔH of binding for said ligand by comparing said plurality of binding affinity values, wherein said ΔH is positive if said binding affinity values increase with increasing temperature, and said ΔH is negative if said binding affinity values decrease with decreasing temperature; and, selecting as lead ligands those candidate ligands in which said ΔH is negative.

2. The method of claim 1 wherein said macromolecule is selected from the group consisting of proteins, peptides, nucleic acids, carbohydrates, and receptor molecules.

3. The method of claim 1 wherein said ligands are selected from the group consisting of proteins, peptides, nucleic acids, carbohydrates, enzyme substrates, and enzyme inhibitors.

4. The method of claim 1 wherein said step of exposing is carried out in a vessel selected from the group consisting of multi-well plates, capillary tubes, etched channels, solid supports, and cuvettes.

5. The method of claim 1 wherein said macromolecule is immobilized in a vessel.

6. The method of claim 1 wherein said step of measuring is carried out by detecting changes in a parameter selected from the group consisting of fluorescence, luminescence, emission, absorption, radioactivity, fluorescence resonance energy transfer, pH, enzymatic activity, molecular weight, and antibody binding.

7. The method of claim 1 wherein said step of exposing is carried out at three or more temperatures.

8. The method of claim 1 further comprising the step of calculating a magnitude of ΔH for each ligand.

* * * * *

UNITED STATES PATENT AND TRADEMARK OFFICE
CERTIFICATE OF CORRECTION

| | |
|---|---|
| PATENT NO. | : 6,242,190 B1 |
| APPLICATION NO. | : 09/451837 |
| DATED | : June 1, 2001 |
| INVENTOR(S) | : Freire et al. |

It is certified that error appears in the above-identified patent and that said Letters Patent is hereby corrected as shown below:

In column 4 at lines 32 should read --The methods here are based on the premise that ligands that bind to the target with lower affinity at higher temperatures are characterized by negative binding enthalpies (exothermic), whereas ligands that bind to the target with higher affinity at higher temperatures are characterized by positive binding enthalpies (endothermic).--; and In column 7 at lines 48-50 should read --As expected, the binding affinity decreases at higher temperatures for the exothermic inhibitor and increases for the endothermic inhibitor.--

In the claims, a typographic error occurred in Claim 1 (column 8, lines 25-28 should read) as follows:

"and said $\Delta H$ is negative if said binding affinity values decrease with decreasing temperature" should be replaced by --and said $\Delta H$ is negative if said binding affinity values decrease with increasing temperature--

Signed and Sealed this

Thirteenth Day of May, 2008

JON W. DUDAS
*Director of the United States Patent and Trademark Office*